United States Patent
Rohde

(10) Patent No.: US 12,303,625 B2
(45) Date of Patent: May 20, 2025

(54) METHOD FOR EXTRACORPOREAL BLOOD PURIFICATION AND DIALYSATE DISPOSAL

(71) Applicant: B. BRAUN AVITUM AG, Melsungen (DE)

(72) Inventor: Alexander Rohde, Melsungen (DE)

(73) Assignee: B. Braun Avitum AG, Melsungen (AG)

(*) Notice: Subject to any disclaimer, the term of this patent is extended or adjusted under 35 U.S.C. 154(b) by 987 days.

(21) Appl. No.: 17/369,127

(22) Filed: Jul. 7, 2021

(65) Prior Publication Data

US 2021/0330551 A1     Oct. 28, 2021

Related U.S. Application Data

(63) Continuation of application No. 16/039,971, filed on Jul. 19, 2018, now abandoned.

(30) Foreign Application Priority Data

Jul. 20, 2017 (DE) ..................... 10 2017 116 394.8

(51) Int. Cl.
*A61M 1/14* (2006.01)
*A61J 1/10* (2006.01)
(Continued)

(52) U.S. Cl.
CPC .................. *A61M 1/14* (2013.01); *A61J 1/10* (2013.01); *A61J 1/1475* (2013.01);
(Continued)

(58) Field of Classification Search
CPC .......... A61J 1/10; A61J 1/1475; A61J 1/2003; A61M 1/3621; B01D 61/30
See application file for complete search history.

(56) References Cited

U.S. PATENT DOCUMENTS

| 3,515,275 A | 6/1970 | Bowman |
| 3,528,550 A | 9/1970 | Cappelen, Jr. |

(Continued)

FOREIGN PATENT DOCUMENTS

| AU | 2004248985 A1 * | 1/2006 | ............. A61M 1/16 |
| CN | 1141006 A | 1/1997 | |

(Continued)

OTHER PUBLICATIONS

Office Action received in Chinese Application No. 201810802122.0 dated Jun. 15, 2023, with translation, 12 pages.

(Continued)

*Primary Examiner* — Leslie R Deak

(74) *Attorney, Agent, or Firm* — Christopher A. Rothe; CM Law

(57) ABSTRACT

A method for extracorporeal blood purification and dialysate disposal includes the steps of: passing a patient's blood through a dialyzer through a first line, passing dialysate through the dialyzer through a second line so that the dialysate exits the dialyzer as used dialysate, and collecting the used dialysate in a container. The container can include an inlet and an outlet connector, the inlet being fluidly connected to the dialyzer to receive the used dialysate, and the outlet connector being fluidly connected to a sewer line of a sewage system in a sealed manner to discharge the used dialysate directly into the sewage system.

12 Claims, 4 Drawing Sheets

(51) Int. Cl.
  *A61J 1/14* (2023.01)
  *A61J 1/20* (2006.01)
  *A61M 1/16* (2006.01)
  *A61M 1/36* (2006.01)
  *A61M 1/28* (2006.01)

(52) U.S. Cl.
  CPC .......... *A61M 1/1668* (2014.02); *A61J 1/2003* (2015.05); *A61M 1/287* (2013.01); *A61M 1/3621* (2013.01)

(56) References Cited

U.S. PATENT DOCUMENTS

| | | | |
|---|---|---|---|
| 4,316,466 A | 2/1982 | Babb | |
| 4,326,526 A | 4/1982 | Buck et al. | |
| 4,991,743 A | 2/1991 | Walker | |
| 5,281,202 A | 1/1994 | Weber et al. | |
| 5,685,385 A | 11/1997 | Sanuga | |
| 5,685,835 A * | 11/1997 | Brugger .......... | A61M 1/362262 422/28 |
| 5,713,850 A | 2/1998 | Heilmann et al. | |
| 5,722,947 A | 3/1998 | Jeppsson et al. | |
| 5,954,951 A | 9/1999 | Nuccio | |
| 6,039,060 A | 3/2000 | Rower | |
| 6,039,718 A * | 3/2000 | Niedospial, Jr. .......... | A61J 1/10 604/408 |
| 6,310,151 B1 | 10/2001 | Windisch et al. | |
| 6,558,340 B1 | 5/2003 | Traeger | |
| 8,025,173 B2 | 9/2011 | Michaels | |
| 8,226,595 B2 | 7/2012 | Childers et al. | |
| 8,460,544 B2 | 6/2013 | Völker | |
| 9,033,948 B2 * | 5/2015 | Payrat .................. | A61M 1/3693 604/408 |
| 9,717,837 B2 | 8/2017 | Vincent | |
| 10,238,855 B2 | 3/2019 | Weber et al. | |
| 10,252,856 B2 | 4/2019 | Michaels et al. | |
| 2003/0230340 A1 | 12/2003 | Anderson et al. | |
| 2004/0036185 A1 | 2/2004 | Garcia | |
| 2004/0267183 A1 | 12/2004 | Chevallet | |
| 2005/0001110 A1 | 1/2005 | Simon | |
| 2009/0182263 A1 | 7/2009 | Burbank et al. | |
| 2009/0204080 A1* | 8/2009 | Balteau .................. | A61M 5/162 604/249 |
| 2010/0006048 A1 | 1/2010 | Minty et al. | |
| 2013/0006171 A1* | 1/2013 | Griessmann .......... | A61M 1/166 604/29 |
| 2014/0232020 A1 | 8/2014 | Sabadicci et al. | |
| 2014/0238912 A1 | 8/2014 | Vincent | |
| 2014/0378915 A1 | 12/2014 | Wesseler | |
| 2015/0224245 A1 | 8/2015 | Payrat et al. | |
| 2016/0008224 A1 | 1/2016 | Rahimy et al. | |
| 2016/0129173 A1 | 5/2016 | Ahrens et al. | |
| 2021/0330551 A1 | 10/2021 | Rohde | |

FOREIGN PATENT DOCUMENTS

| | | |
|---|---|---|
| CN | 1309572 A | 8/2001 |
| CN | 1423576 A | 6/2003 |
| CN | 101437604 A | 5/2009 |
| CN | 101535129 A | 9/2009 |
| CN | 202699702 U | 1/2013 |
| CN | 104225781 A | 12/2014 |
| CN | 209900233 U | 1/2020 |
| DE | 3211895 A1 | 10/1983 |
| DE | 3320416 A1 | 12/1984 |
| DE | 8505923 U1 | 5/1985 |
| DE | 3409457 A1 | 9/1985 |
| DE | 3911587 A1 | 10/1990 |
| DE | 19528160 A1 | 1/1997 |
| DE | 19537271 A1 | 4/1997 |
| DE | 202004016882 U1 | 1/2005 |
| DE | 60310935 | 10/2007 |
| DE | 102009038574 A1 | 3/2011 |
| DE | 102009038571 | 7/2011 |
| DE | 102009038571 B | 7/2011 |
| DE | 102013106550 A1 | 12/2014 |
| DE | 202016000643 U1 | 3/2016 |
| EP | 0303765 A1 | 2/1989 |
| EP | 0530667 A1 | 3/1993 |
| EP | 0593102 A1 | 4/1994 |
| EP | 0715860 A1 | 6/1996 |
| EP | 2353629 A1 | 8/2011 |
| EP | 2818152 A1 | 12/2014 |
| EP | 3017832 A1 | 1/2017 |
| EP | 3017832 B1 | 1/2017 |
| FR | 2539034 A1 | 7/1984 |
| JP | H09313597 A | 12/1997 |
| JP | H09323597 A | 12/1997 |
| JP | 2010502373 A | 1/2010 |
| JP | 2010522061 A | 7/2010 |
| JP | 2012179432 A | 9/2012 |
| WO | 8810124 A1 | 12/1988 |
| WO | 9520985 A1 | 8/1995 |
| WO | 0164262 A2 | 9/2001 |
| WO | 2009139878 A1 | 11/2009 |
| WO | 2013050689 A1 | 4/2013 |
| WO | 2013055283 A1 | 4/2013 |
| WO | 2013098779 A1 | 7/2013 |
| WO | 2015067359 A1 | 5/2015 |

OTHER PUBLICATIONS

Final Office Action received in U.S. Appl. No. 16/039,971 dated Mar. 30, 2022, 16 pages.
Office Acton received in Chinese Application No. 201810802122.0 dated May 7, 2022, with translation, 26 pages.
Office Action received in Chinese Application No. 201810802122.0 dated Jan. 28, 2023, with translation, 23 pages.
Haemodialysis, MSR Media Supply Rail, flyer of Fresenius Medical Care Deutschland GmbH, 2012, without reservation at the Industrial Exhibition of the 50th ERA-EDTA Congress, May 18-21, 2013, at the ICCC Istanbul Congress Center, 1 page.
Photo of a package surrounding the bag shown in the D10-D13 and D19, multiFiltrate bag with year of manufacture 2015 from the rear side.
Photo of a package surrounding the bag shown in the D10-D13 and D19, multiFiltrate bag with year of manufacture 2015 from the frong side.
Popp, "Law, structure and behavior—experiences from Germany," Presentation Malta, Mar. 13, 2014, 15 pages.
Ronco, et al., "Critical Care Nephrology," Kluwer Academic Publishers, Critical Care Nephrology, published 1998, 53 pages.
Summons to Oral Proceedings received in European Application No. 18184208.9-1113 dated Dec. 20, 2021, with translation, 23 pages.
Acute Therapy Systems, multiFiltratePRO, A perfect fit for every team, Ci-Ca multiIntenseCare, Fresenius Medical Care, Germany, 2015, 20 pages.
Acute Therapy Systems, multiFiltratePRO, Supporting your clinical practice, Ci-Ca multiIntenseCare, Fresenius Medical Care, 2015, 12 pages.
Acute Therapy Systems, Product Range, Fresenius Medical Care, Jul. 2010, 26 pages.
Acute Therapy Systems, The multiFiltrate system: Your choice for optimal therapy, Fresenius Medical Care, 2015, 16 pages.
Baldwin, et al., "Clinical Nursing for the Application of Continuous Renal Replacement Therapy in the Intensive Care Unit," The clinical Application of CRRT—Current Status, Department of Intensive Care, 2009, 5 pages.
Baldwin, et al., "Nursing for Renal Replacement Therapies in the Intensive Care Unit: Historical, Educational, and Protocol Review," Blood Purification, Jan. 14, 2009, 8 pages.
Cruz, et al., "Machines for Continuous Renal Replacement Therapy," The Clinical Application of CRRT—Current Status, Department of Nephrology, 2009, 10 pages.
Extended European Search Report for European Application No. 18 184 208.9, dated Dec. 12, 2018, with translation, 10 pages.

(56) References Cited

OTHER PUBLICATIONS

Fresenius Medical Care: Acute Therapy Systems—Multi Filtrate Ci-Ca Total Solution for Citrate Anticoagulation, Jun. 2014, Sydney, Australia (AP391/AT/AU/2014)—8 pages.

German Search Report for Application No. 10 2017 116 394.8, dated Mar. 5, 2018, with English translation—15 pages.

Office Action received in European Application No. 18184208.9-1113, dated Apr. 22, 2021, with translation, 94 pages.

Office Action received in Japanese Application No. 2018-136673 dated Feb. 3, 2021, with translation, 4 pages.

Ronco, et al., "Continuous Renal Replacement Therapy: Opinions and Evidence," Advances in Renal Replacement Therapy, vol. 9, No. 4., Oct. 2002, 16 pages.

Office Action received in U.S. Appl. No. 16/039,971, filed Jan. 14, 2022, 10 pages.

\* cited by examiner

METHOD FOR EXTRACORPOREAL BLOOD PURIFICATION AND DIALYSATE DISPOSAL

CROSS REFERENCE TO RELATED APPLICATIONS

This application is a continuation of U.S. application Ser. No. 16/039,971, filed Jul. 19, 2018, and claims the benefit of priority of German Application No. 10 2017 116 394.8, filed Jul. 20, 2017. The contents of U.S. application Ser. No. 16/039,971 and German Application No. 10 2017 116 394.8 are incorporated by reference herein.

FIELD

The present invention relates to a disposal container, preferably a sterile disposal container, for used dialysate according to the preamble of the independent claim. Moreover, the invention is directed to an extracorporeal blood purification system, especially dialysis system, according to the preamble of the dependent claims. Generic blood purification systems include a stationary system area, such as a stationary wastewater system, and a non-stationary system area adapted to be selectively connected thereto, such as at least one dialysis machine of the mobile type.

BACKGROUND

Dialysis machines of the mobile type, such as machines for acute dialysis, are used for acute renal failure of a patient in all departments of a hospital, especially in an intensive care unit. Here a quick/dynamic availability for use of the dialysis machine is an important criterion; therefore, prefabricated dialyzing solutions are arranged on the dialysis machine. The used dialysate, i.e. the dialysate which has been prepared by the dialysis machine and has passed through a dialyzer for blood purification of a patient, in dialysis machines of the mobile type is collected in a (sterile) disposal container consisting of a bag such as a reject bag. The latter is sealed against the environment in a preferably sterile manner so that also the used dialysate is sealed against the germ-intensive environment such as e.g. the intensive care unit.

After or—depending on the volume of the bag—also during treatment a bag filled with used dialysate is disposed of. The bag is initially put/thrown into a sink so that the content of the bag, i.e. the used dialysate, will flow into a sewage system of the respective hospital. After that, the empty bag, i.e. the bag wrapping emptied from dialysate, is supplied to a special refuse system. Said special refuse system has to be treated separately from the other refuse; therefore, the disposal thereof entails comparatively high cost.

In practice it has been observed that in the drain, namely, when the bag wrapping contaminated by the germ-intensive hospital environment contacts the draining used dialysate, the dialysate discharged into the sewage system is loaded with additional germs. In this way, e.g. pathogenic germs which usually would have to be disposed of via the aforementioned special refuse system may happen to enter into the sewage system of a hospital.

DESCRIPTION OF THE RELATED ART

In order to stop such risk, in the state of the art the bags that are emptied in appropriate sinks in which mixing with germs caught in the intensive care unit, for example, is possible are discharged including the bag content thereof, i.e. the bag wrapping plus used dialysate, in a special refuse system.

It is a drawback of said solution that the disposal of the special refuse with an increasing weight involves increased financial expenditure. In addition, the disposal of completely filled bags poses a risk of leakage of a bag, thus causing the used dialysate to spread in the special refuse showing the perversities of a liquid.

SUMMARY

In view of said state of the art, an object underlying the present invention is to eliminate or at least alleviate the drawbacks known from the state of the art and, especially, to drain the bag content, namely, the used dialysate, into the sewage system instead of into the special refuse system, while avoiding the risk of a mixing with germs present on the surface of the bag, however.

According to aspects of the invention, this object is achieved by a preferably sterile disposal container comprising the features of the independent claim. In order to be able to efficiently integrate such disposal container/bag, which is a single-use article, in a hospital environment, also an extracorporeal blood purification system according to the dependent claims is an aspect of the inventive idea. Advantageous embodiments are the subject-matter of the subclaims.

From said configuration of the bag as well as an extracorporeal blood purification system according to aspects of the invention, for example the following advantages can be derived:
  increased hygienic standard due to the suppressed possibility of contamination of the used dialysate;
  an ergonomic advantage for the users of the blood purification system due to the temporary short circuit between the bag and the sewage system;
  an economic advantage due to the decrease of special refuse costs.

Accordingly, the subject matter of the invention is a preferably sterile disposal container for used dialysate comprising (e. g. consisting of) a flexible bag in or at which an inlet connection for receiving the used dialysate is formed or arranged. The inlet connection is prepared for connecting the bag to a dialysis machine of the mobile type, i.e. an "acute machine". It is resulting herefrom that the e.g. sterile disposal container can be moved or displaced along with the dialysis machine so that the acute machine can be employed in many places without high expenditure.

According to aspects of the invention, the disposal container/bag includes an outlet connection or connector that is provided separately from the inlet connection and is prepared for connecting the bag to a sewer line present in the hospital environment in a way sealed against the connector environment so that no exchange is possible between the interior of the connector and the exterior of the connector. As part of the inventive idea, the bag can be connected by means of a connector to the sewer line (of the sewage system) such that the used dialysate present in the bag, i.e. caught/received by the bag can be discharged via the sewer line from the blood purification system and later from the hospital. In this way, the bag content, i.e. the used dialysate, can be achieved to flow immediately and directly into the sewage system without taking up potential germs of the bag surface before. Thus, the risk of undesired contamination of the sewer flow is eliminated.

The invention equally comprises an extracorporeal blood purification system including a stationary system area which has at least one sewer line of a sewage system and including a non-stationary system area which has at least one blood purification machine. Such blood purification machine makes available dialysate which is prepared to pass through a dialyzer so as to purify e.g. the blood of a patient in this way. After passing through the dialyzer, the blood purification machine guides the used dialysate further into/to the bag which is preferably designed as a single-use reject bag.

In other words, the invention can be functionally described so that the non-stationary system section of the blood treatment system is operatively connected to the stationary system area such that the (non-stationary) bag content communicates with the (stationary) sewage system without any bypass and without any further element/step being interconnected.

In terms of structure, it is a fact that a bridging between the (non-stationary) bag and the (stationary) sewer line is realized by means of a connector which is arranged/applied/ taken into operation/laid by a user, preferably at the beginning of the acute dialysis.

Apart from the advantage of avoiding germ transmission into the sewage system, the solution according to aspects of the invention also makes open emptying of bags such as reject bags superfluous. The splashes and turbulences resulting herefrom, which in turn stain the sink with the used dialysate, will no longer occur according to aspects of the invention, thus causing the hygienic standard in a hospital to be further increased.

Of preference, the connector ensuring such bridging is configured to be integral/made of one material with the bag. In this way, possible transmission of the pathogenic germs, for example from the intensive care unit, into the interior of the bag and thus into the sewer line is excluded from the start, thus allowing maximum medical hygiene regulations to be observed without any additional effort. In addition, the connector includes, at its end facing away from the bag, a connection, preferably in the form of a Luer lock or a three-way cock or a Walther coupling, so as to safely and time-efficiently couple the same with the sewer line. A Walther coupling is a connection system in which a fixed coupling part is moved with respect to a coupling part displaceable in portions relative to the longitudinal axis of the connection so as to cause coupling and, respectively, uncoupling. Depending on the embodiment, the fixed coupling part is provided on the connection side or alternatively on the sewer line side and the displaceable coupling part is complementary to the fixed one.

As an alternative to the integral configuration, the connector may as well be in the form of an external component, i.e. a component that is separate from the bag in terms of material and/or space. The connector as an external component in turn includes a bag connection so as to be adapted to be coupled/connected to the bag. All connecting mechanisms for connecting a tube (connector) to a bag are considered as bag connector. The bag connector itself can be designed both integrally in one material piece with the connector and as an external component, i.e. as a component that is separate from the connector in terms of material and/or space. In this embodiment, too, at its end facing away from the bag the connector includes a connection, preferably in the form of a Luer lock or a three-way cock or a Walther coupling. Thus, also in this embodiment it can be safely and time-efficiently coupled to the sewer line.

In the afore-mentioned bag connection especially an inserting pin, also referred to as spike, can be used. An inserting pin has a hollow tip, usually chamfered, which is prepared to pierce the bag. Further, it includes a seat defining a predefined stop surface of the inserting pin relative to the bag so that the inserting depth of the inserting pin is predetermined by means of the geometry. The inserting pin is surrounded, at its tip, by a wrapping which is removed as late as immediately before piercing of the bag, thus avoiding the risk of contamination of the bag content by the tip of the inserting pin. It is an advantage of the configuration of the bag connection in the form of an inserting pin that conventional blood purification systems having no specifically formed bags in accordance with the invention may be retrofitted.

Alternatively to the configuration as an inserting pin, the bag connection can also be realized as a Luer lock. In this case, the inner cone is formed by the bag and the outer cone is formed by the connector. Vice versa, it is also imaginable to form the outer cone by the bag and to form the inner cone by the connector. The Luer lock excels by a high degree of reliability, thus excluding contamination of the bag content.

As an alternative to the Luer lock, apart from a drain coupling, also a bag-side coupling by means of a Walther coupling is imaginable. In this context, the fixed coupling part can be selectively attached to the bag or to the connector. The movable coupling part displaceable in the longitudinal direction relative to the fixed coupling part (the travel distance of which enables coupling and uncoupling) is configured to be appropriately complementary to the fixed coupling part.

In an advantageous embodiment, the connector of the extracorporeal blood purification system includes another so-called auxiliary connection via which the connector can be coupled to an auxiliary (water) line. Said auxiliary line advantageously guides water inside itself and toward the connector so that by means of pressurization it ensures an increased emptying rate of the dialysate out of the bag into the sewer line. In this way, while exploiting the principles of flow according to Bernoulli and Venturi, an objective is pursued that immediately after having been used at a first place a dialysis machine of the mobile type can be reused at another place, as due to pressurization emptying of the bag is performed in no time at all.

Moreover, it is imaginable to provide the extracorporeal blood purification system according to aspects of the invention with a folding mechanism which is prepared to transmit a compressing force to the bag so as to reduce the volume thereof and thus to ensure an increased emptying rate of the dialysate out of the bag into the sewer line with pressurization. Accordingly, a change of volume is employed instead of a change of flow (as shown in the afore-presented embodiment) so as to reach a maximum emptying rate.

Furthermore, a preferred embodiment excels by the fact that the bag is surrounded at least in part/in portion by/with an outer packaging/wrapping/packaging so that by such outer packaging an additional sterile barrier is realized between the environment and the outer surface of the bag. This increases the safety of the extracorporeal blood purification system according to aspects of the invention by the fact that pathogenic germs are additionally hindered from contaminating the bag. Said outer packaging is (equally) disposed of via the special refuse of a hospital, with the contamination thereof thus causing no hygienic problems for the refuse disposal.

It is in addition advantageous when the connector is at least in part/in portion surrounded by a movable housing and said housing is displaced as late as immediately before connecting the connector to the bag so that the housing constitutes an additional sterile barrier between the environment and the connector. This, too, increases the safety of the extracorporeal blood purification system according to aspects of the invention by the fact that pathogenic germs are additionally hindered from contaminating the bag. Said housing is (equally) disposed of via the special refuse of a hospital, with the contamination thereof thus causing no hygienic problems for the refuse disposal.

Moreover, in a preferred embodiment the sewer line of the sewage system is a supply and/or discharge line of a stationary blood purification system, preferably of a blood purification system for chronical dialysis treatment. Hence the advantages of a dialysis machine of the mobile type for acute treatment, i.e. a mobile place of use, are combined with the advantages of a dialysis machine of the stationary type for chronical dialysis treatment, i.e. an established sewage system.

BRIEF DESCRIPTION OF THE DRAWINGS

The invention is best understood from the following detailed description when read in connection with the accompanying drawings. Included in the drawings are the following figures.

DETAILED DESCRIPTION

Figure 1:
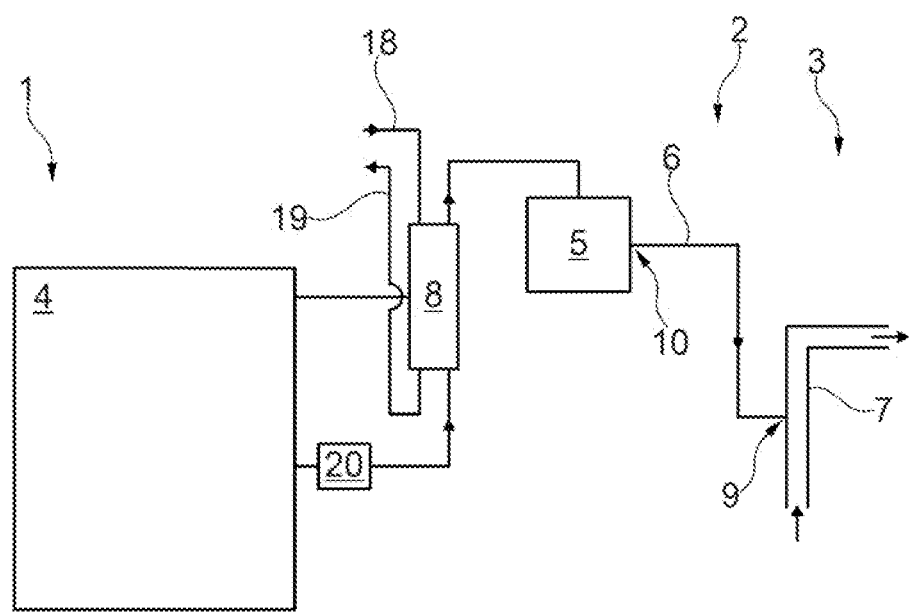
FIG. 1 shows an extracorporeal blood purification system according to aspects of the invention in schematic representation.

FIG. 1 illustrates an extracorporeal blood purification system 1. It includes a non-stationary system area 2 which incorporates, for example, a dialysis machine 4, preferably of the mobile type. Apart from that, the extracorporeal blood purification system 1 includes a stationary system section 3 incorporating, for example, the stationary lines of a sewage system such as a sewer line 7. The non-stationary system section 2 may also include—unlike the representation in FIG. 1—plural dialysis machines which then are connected to the sewer line 7 via plural connections.

As a substantial component of the invention, a bag 5 such as a single-use reject bag, a so-called disposable, is connected downstream of a dialyzer 8. In the bag 5 thus dialysate used by a dialysis is collected. A connector 6 is arranged as a bridge between the non-stationary system area 2 and the stationary system area 3 and enables the used dialysate to be transferred/transmitted/forwarded from the bag 5 into the sewer line 7. Thus, the bag 5 is emptied in due time and directly with the connector 6 and the sewer line 7 and need not be transmitted to an external sink but has to be discharged directly into the special refuse after completion of the dialysis. In this way, possible contamination in both directions—i.e. both by germs in the environment to the used dialysate and thus into the sewer system and by the used dialysate into the environment—is prevented.

The connector 6 is connected to the bag 5 via a bag connection 10. Individual embodiments of the bag connection 10 will be illustrated in detail in connection with FIGS. 2a, 2b, 2c. At the other end of the connector 6 a connection 9 facing away from the bag is arranged. Said connection ensures safe inexpensive and time-efficient connection of the connector 6 to the sewer line 7. As examples of the connection 9 facing away from the bag, a Luer lock 12 or a three-way cock or a Walther coupling are mentioned.

The basic functioning of an extracorporeal blood purification system 1 of the generic type, namely that blood from a patient is supplied via a first line 18 to the dialyzer 8, preferably being operated by the counter-flow principle, where it is purified and returned to the patient again via a second line 19, is known so that in this respect the state of the art is referred to. It is merely worth mentioning in this context that the extracorporeal blood purification system 1 includes a pump 20 which delivers the fresh dialysate to the dialyzer 8 and from there delivers the used dialysate further into the bag 5.

Figure 2A:
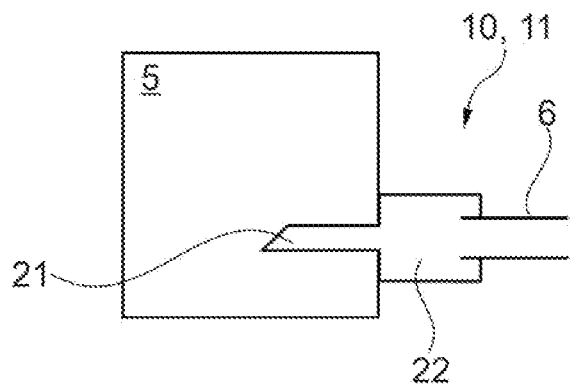
FIG. 2a shows a bag comprising a connector in a first embodiment.

With reference to FIG. 2a, a first embodiment of the bag connection 10 is presented. An inserting pin 11 here makes the connection between the bag 5 and the connector 6. The inserting pin is divided into a tip 21 and a seat 22. While the tip 21 is prepared to pierce the bag 5, the seat 22 ensures a stop, i.e. safe contact of the inserting pin 11 with the bag 5. The inserting pin 11 is either formed integrally with the connector 6 or is attached to the latter as an additional part.

Figure 2B:
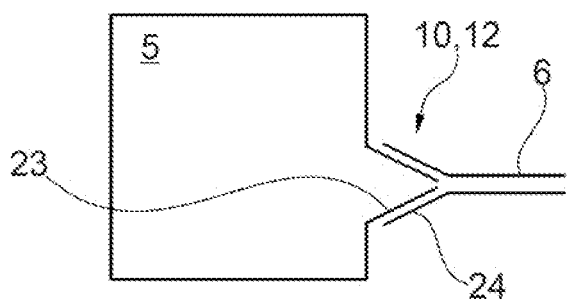
FIG. 2b shows a bag comprising a connector in a second embodiment.

FIG. 2b shows another option of the bag connection 10. Here the bag connection 10 is realized as a Luer lock 12 (alternatively also a Walther coupling would be imaginable, as mentioned already). In this way, the bag 5 forms an inner cone 23 to which an outer cone 24 formed by the connector 6 is attached so as to realize a secure connection between the bag 5 and the connector 6. The outer cone 24 is either formed integrally with the connector 6 or is attached to the latter as an additional part.

Figure 2C:
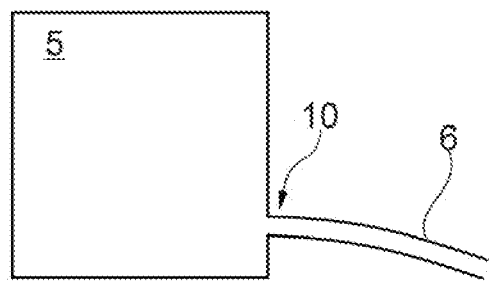
FIG. 2c shows a bag comprising a connector in a third embodiment.

A third option of the bag connection 10 is finally illustrated in FIG. 2c. In this case, the bag 5 integrally includes the bag connection 10. In this way, the connector 6 and the bag 5 are configured as one component part, thus entailing logistic advantages as the bag connection 10 no longer needs to be mounted later.

Figure 3A:
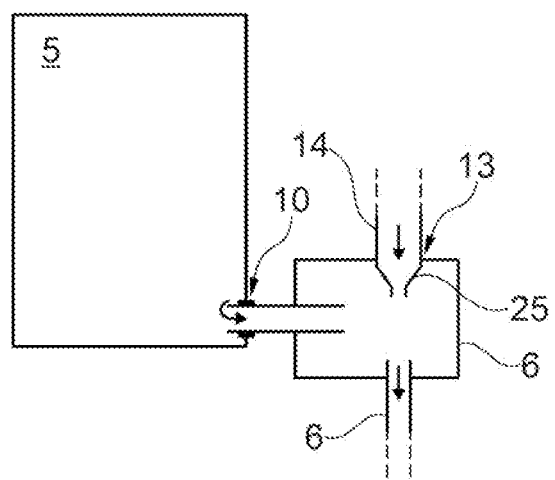
FIG. 3a shows a bag comprising a connector in another embodiment.

Another embodiment of the interaction of the bag 5 and the connector 6 is shown in FIG. 3a. In this case, the connector 6 is coupled to an auxiliary line 14 via an auxiliary connection 13 and thus realizes a water jet pump. The auxiliary line 14 primarily guides water along the direction of flow as shown with the upper arrow. Due to the tapering 25 of the auxiliary line 14, an increase in the flow rate of the water guided in the auxiliary line 14 is reached, thus entailing a pressure drop (Bernoulli). Said pressure drop results in "suction" of the used dialysate out of the bag 5 (see arrow in the bag 5), which results in quick and efficient emptying of the bag 5. With the embodiment comprising the auxiliary connection 13 and the auxiliary line 14, accordingly quick emptying of the bag 5 is achieved. The connector 6 further includes a line (see lower arrow) which conveys the mixture of used dialysate (from the bag 5) and water (from the auxiliary line 14) in the direction of the sewer line 7 (see FIG. 1). Said line can be configured either as an integral part of the connector 6 or as an additional component.

Figure 3B:
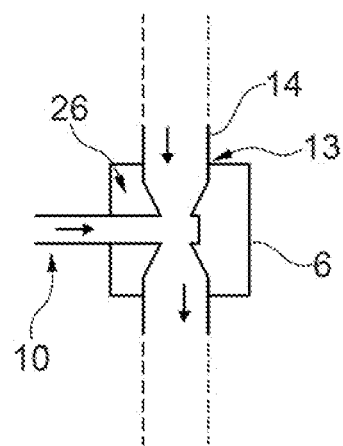
FIG. 3b shows a connector in another embodiment shown per se.

FIG. 3b illustrates a similar functional principle with an auxiliary line 14 and an auxiliary connection 13. Deviating from FIG. 3a, here a Venturi nozzle 26 is inserted. The active principle of the Venturi nozzle 26 can equally be traced back to Bernoulli and therefore is not explained in more detail in this context—because this has already been done in connection with FIG. 3a.

Figure 4:
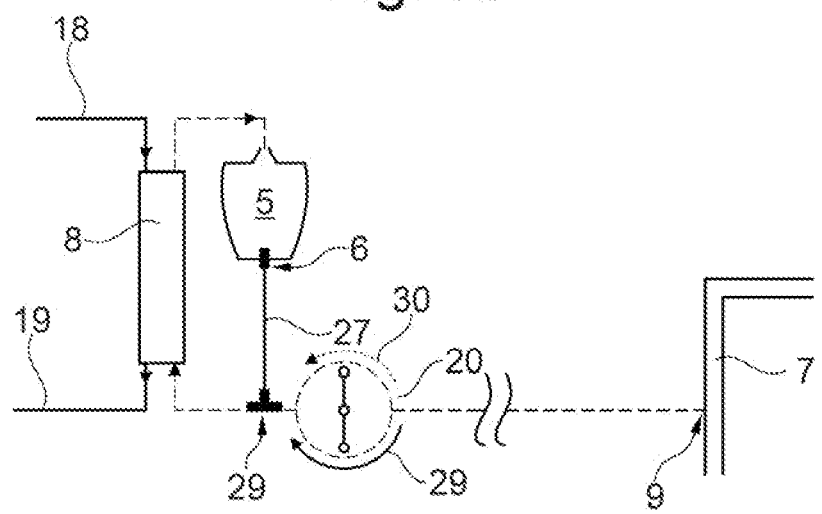
FIG. 4 shows another embodiment of the blood purification system according to aspects of the invention.

FIG. 4 illustrates another embodiment of the invention in which the pump 20 is indicated as a peristaltic pump. The connector 6 is coupled to the sewer line 7 while interconnecting a bridge line 27 and a dialysate line 28. For this purpose, a three-way cock 29 is arranged. In a first state in which the dialysis is carried out, the three-way cock 29 is in such position that no fluid is delivered through the bridge line 27. The pump 20 rotates along the first delivery direction 29. When viewing the schematically represented configuration in FIG. 4, it is evident that an inlet connection is preferably arranged in the upper area of the bag 5.

As soon as the dialysis is completed, the three-way cock 29 is turned so that the path between the bridge line 27 and the line in which the pump 20 is disposed is released. In this state, the pump is reversed, namely, along the second delivery direction 30. Thus, with the aid of the pump capacity of the pump 20 a delivery of the used dialysate out of the bag 5 toward the sewer line 7 is enabled.

Figure 5:
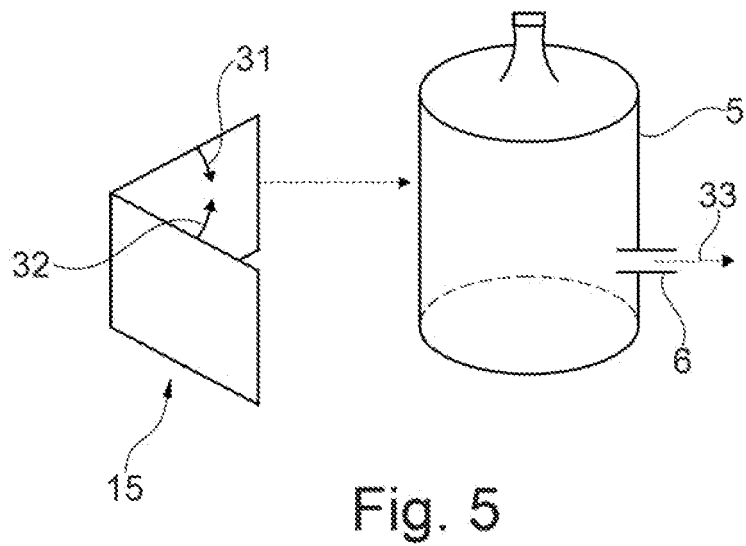
FIG. 5 shows a schematically represented bag including a folding mechanism.

In FIG. 5, a further mechanism for emptying the bag 5 is disclosed. In contrast to the afore-presented mechanisms generating a vacuum, in this case a folding mechanism 15 is used to reduce the bag volume by mechanical force from outside. In the merely schematically indicated folding mechanism 15 of FIG. 5, two pivot arrows 31, 32 are visible which crush the bag 5 in the manner of an aluminum can being compressed in the recycling operation so as to force the volume flow along the arrow 33. This guarantees quick emptying of the bag 5.

Figure 6:
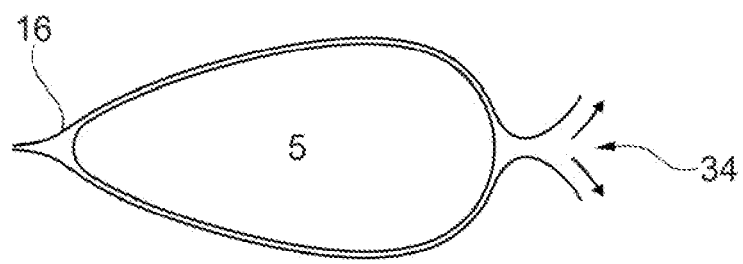
FIG. 6 shows a bag in another embodiment.

FIG. 6 schematically represents a bag 5 which is surrounded by an outer packaging 16 realizing an additional sterile barrier. The outer packaging 16 includes an open constriction 34 at which an operator may release the outer packaging 16 by means of an opposite movement. This prevents contamination of the outer surface of the bag 5.

Figure 7:
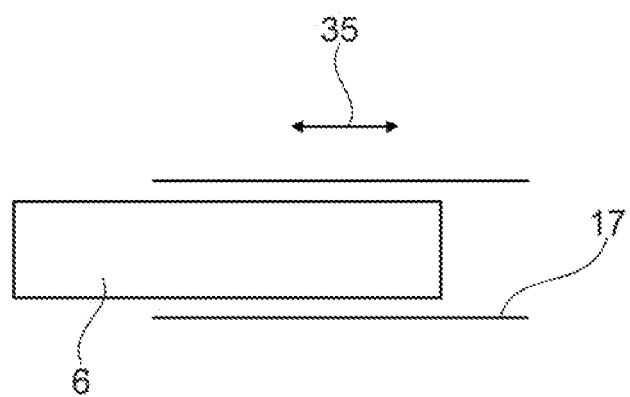
FIG. 7 shows a connector in another embodiment.

FIG. 7 shows an embodiment in which a housing 17 is arranged around the connector 6. The housing 17 may surround the connector 6 completely or else only partly. Along a sliding movement 35 the housing 17 is displaceable relative to the connector 6, for example against the bias of a spring. Thus, it is possible that the connector 6, for example in the embodiment in which it is configured as inserting pin 11 (see FIG. 2a), contacts the ambient air to which germs are complexed as late as immediately before piercing/inserting, thus causing an additional sterile barrier which further increases the hygienic standards reached by the solution according to aspects of the invention to be realized by means of the housing 17.

The invention claimed is:

1. A method for extracorporeal blood purification and dialysate disposal, the method comprising the steps of:
    passing a patient's blood through a dialyzer through a first line;
    passing dialysate through the dialyzer through a second line so that the dialysate exits the dialyzer as used dialysate;
    collecting the used dialysate in a container, the container comprising an inlet and an outlet connector, the inlet being fluidly connected to the dialyzer to receive the used dialysate, and the outlet connector being fluidly connected to a sewer line of a sewage system in a sealed manner to discharge the used dialysate directly into the sewage system; and
    discharging the used dialysate through the outlet connector and into the sewage system,
    wherein the step of discharging the used dialysate through the outlet connector and into the sewage system comprises the step of inducing a pressure gradient between the container and the outlet connector to remove the used dialysate from the container,
    wherein the step of inducing a pressure gradient between the container and the outlet connector to remove the used dialysate from the container comprises inducing a pressure drop in the outlet connector to remove the used dialysate from the container by suction, and
    wherein the outlet connector is attached to an auxiliary line that delivers a water jet into the outlet connector.

2. The method of claim 1, wherein the sewer line is located in a hospital, and the dialyzer is connected to a mobile dialysis machine that is movable to different treatment locations in the hospital.

3. The method of claim 1, wherein the container comprises a flexible bag.

4. The method of claim 1, wherein the outlet connector comprises a connection that connects the outlet connector to the container.

5. The method of claim 4, wherein the connection comprises an inserting pin, the inserting pin having a tip configured to pierce the container.

6. The method of claim 4, wherein the connection comprises a Luer lock or Walther coupling.

7. The method of claim 4, wherein the connection is integrally formed with the container as one piece.

8. The method of claim 1, wherein the auxiliary line comprises a tapered section, and wherein the step of inducing a pressure drop in the outlet connector comprises delivering water through the tapered section to create the pressure drop and remove the used dialysate from the container by suction.

9. The method of claim 1, wherein the outlet connector comprises a Venturi nozzle, and wherein the step of inducing a pressure drop in the outlet connector comprises delivering water through the Venturi nozzle to create the pressure drop and remove the used dialysate from the container by suction.

10. The method of claim 1, wherein the step of discharging the used dialysate through the outlet connector and into the sewage system is carried out until the container is empty.

11. The method of claim 10, further comprising the step of disposing of the container after the container is empty.

12. The method of claim 11, wherein the step of disposing of the container after the container is empty comprises removing the container from an outer packaging that acts as a sterile barrier around the container while the container collects the used dialysate.

* * * * *